(12) United States Patent
Lee et al.

(10) Patent No.: US 7,563,467 B2
(45) Date of Patent: Jul. 21, 2009

(54) **USE OF AN *OPUNTIA FICUS-INDICA* EXTRACT AND COMPOUNDS ISOLATED THEREFROM FOR PROTECTING NERVE CELLS**

(75) Inventors: Yong Sup Lee, Seoul (KR); Hokoon Park, Seoul (KR); Changbae Jin, Seoul (KR); Hyoung Ja Kim, Seoul (KR); Jungsook Cho, Kyungju-si (KR); Mijeong Park, Daejon (KR); Yunaaon Song, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 181 days.

(21) Appl. No.: 10/493,748

(22) PCT Filed: Oct. 29, 2002

(86) PCT No.: PCT/KR02/02010

§ 371 (c)(1),
(2), (4) Date: Oct. 12, 2004

(87) PCT Pub. No.: WO03/037324

PCT Pub. Date: May 8, 2003

(65) Prior Publication Data

US 2005/0042311 A1    Feb. 24, 2005

(30) Foreign Application Priority Data

Oct. 29, 2001    (KR) .................. 10-2001-0066810

(51) Int. Cl.
*A61K 36/33* (2006.01)
(52) U.S. Cl. .................. 424/767; 424/777; 424/779
(58) Field of Classification Search .................. 424/767
See application file for complete search history.

(56) References Cited

U.S. PATENT DOCUMENTS 3,860,710 A    1/1975    Giovanozzi-Sermanni et al.
5,972,923 A *  10/1999    Simpkins et al.

FOREIGN PATENT DOCUMENTS

| JP | 61-085324 A | 4/1986 |
| JP | 10-059995 A | 3/1998 |
| KR | 2001-0072146 A | 7/2001 |
| RU | 2090205 C1 * | 9/1997 |
| WO | WO00/07581 | 2/2000 |

OTHER PUBLICATIONS

Laekeman, G. M. et al. Planta Medica (1986), 6: 433-437. Cardiovascular effects of 3-Methylquercetin.*
Plotnikov, M. B. et al. Bulletin of Experimental Biology and Medicine (Nov. 2000), 130(11): 1080-3. Cerbroprotective effects of diquertin and ascorbic acid.*
El-Moghazy, A. M. et al. Egyptian Journal of Pharmaceutical Sciences (1982), 23(1-4): 247-254. A Phytochemical Study of *Opuntia ficus indica* (L.) Mill cultivated in Egypt.*
Jeong, S. J. et al. Saengyak Hakhoechi (1999), 30(1): 84-86. Flavonoids from the fruits of *Opuntia ficus-indica* var. *saboten*.*
Park, E.-H. et al. Fitoterpia (Feb. 2001), 72(2): 165-167. Wound healing activity of *Opunta ficus-indica*.*
Green, J. The Herbal Medicine-Maker's Handbook: A Home Manual, 2000. The Crossing Press, U.S.A. Chapter 5: The Extraction Process, pp. 74-77; and, Chapter 6: Solvents, pp. 80-98.*
Pavia, D.L. et al., Introduction to Organic Laboratory Techniques, Third edition, 1988. Saunders College Publishing, U.S.A. Chapter Technique 5: Extraction, The Separatory Funnel, Drying Agents, pp. 541-550.*
Pearce, K. A. American Family Physcian (2000), 62 (6). Update on vitamin Supplements for the prevention of coronary disease and stroke.*
Lipids OnLine (Aug. 14, 2007). No clear antioxidant benefit in CVD prevention among high-risk women. Downloaded on Aug. 20, 2007.*
Mattson, M. Aug. 2004. Nature, vol. 430: 631-639. Pathways towards and away from Alzheimer's disease.*
Cosentino, M. et al. BMC Health Services Research (Mar. 24, 2005; 5(1): 26. Medical healthcare use in Parkinson's disease: Survey in a cohort of ambulatory patients in Italy.*
Eberling et al. Experimental Neurology (2002), vol. 178: 236-242. The immunophilin ligand GPI-1046 does not have neuroregenerative effects in MPTP-treated monkeys.*
Emborg, M. E. Journal of Neuroscience Models (2004), vol. 139: 21-143. Evaluation of animal models of Parkinson's disease for neuroprotective strategies.*
Wie, Myoung-Bok. Yakhak Hoeji (Dec. 2000); 44(6): 613-619. Protective effects of *Opuntia ficus-indica* and *Saururus chinensis* on free radical-induced neuronal injury in mouse cortical cell cultures.*
Translation of J. Pharm. Soc. Korea (Dec. 2000); 44(6); "Protective effects of *Opuntia ficus-indica* and *Saururus chinensis* on free radical-induced neuronal injury in mouse cortical cell cultures" by Myung-Bok Wie. Translated by Schreiber Translations, Inc.*
Danglels, O et al. Journal of the Chemical Society-Perkin Transactions 2; (1999); 7: 1387-1395. One-electron oxidation of quercetin and quercetin derivatives in protic and non protic media.*
Wei, M-B. Yakhak Hoeji (Dec. 2000), 44(6): 613-619. Protective effects of *Opuntia ficus-indica* and *Saururus chinensis* on free radical-induced neuronal injury in mouse cortical cell cultures.*
PTO XX-XXXX. Translation of Wei, M-B: "Protective effects of *Opuntia ficus-indica* and *Saururus chinensis* on free radical-induced neuronal injury in mouse cortical cell cultures".*
Cimanga, K et al. Journal of Pharmacy and Pharmacology (2001), 53: 757-761. Radical scavenging and xanthine oxidase inhibitory activity of phenolic compounds from *Bridelia ferruginea* stem bark.*

(Continued)

*Primary Examiner*—Michele Flood
(74) *Attorney, Agent, or Firm*—Finnegan, Henderson, Farabow, Garrett & Dunner, LLP

(57) ABSTRACT

An ethyl acetate extract of *Opuntia ficus-indica* and compounds isolated therefrom for preventing and treating brain diseases such as Alzheimer's disease, stroke and Parkinson's disease, cell and tissue damage caused by ischemia, or cardiovascular system disease such as myocardial infarction.

14 Claims, 7 Drawing Sheets

OTHER PUBLICATIONS

Arcoleo, A et al.. Atti Accad. Sci. Letters Arti Palermo Pt. 1 (1962), 22: 115-18. Flavonoid pigments from family opuntiae, II. The structure of a flavonoid gludoside from *Opuntia ficus-indica*.*

An Tok-Kyun, "Cactus," Illustrated Book of Korean Medicinal Herbs, Soul: Kyohaksa, 497 (1998).

Galati et al., "Antiulcer activity of *Opuntia ficus indica* (L.) Mill. (Cactaceae): ultrastructural study," J. Ethnopharmacol., 76: 1-9 (2001).

Lee, N.H. et al., "Screening of the Radical Scavenging Effects, Tyrosinase Inhibition and Anti-allergic Activities Using *Opuntia ficus-indica*," Kor. J. Pharmacogn., 31(4): 412-415 (2000).

Trejo-González et al., "A purified extract from prickly pear cactus (*Opuntia fuliginosa*) controls experimentally induced diabetes in rats," J. Ethnopharmacol., 55: 27-33 (1996).

International Search Report of PCT/KR02/02010.

International Preliminary Examination Report of PCT/KR02/02010.

Park Eun-Hee et al. "Studies on the pharmacological actions of cactus: identification of its anti-inflammatory effect", Arch. Pharmacal Res., 21(1): 30-34 (1998).

* cited by examiner

USE OF AN *OPUNTIA FICUS-INDICA* EXTRACT AND COMPOUNDS ISOLATED THEREFROM FOR PROTECTING NERVE CELLS

FIELD OF THE INVENTION

The present invention relates to a use of an ethyl acetate extract of *Opuntia ficus-indica* and compounds isolated therefrom for protecting neurons.

BACKGROUND OF THE INVENTION

When the blood flow through the cerebral artery or coronary artery is reduced below a threshold value e.g., by the blocking action of thrombosis or arteriosclerosis, the resulting ischemia damages cerebral nerve or cardiac cells, leading to brain or myocardial infarction due to cell death. Brain ischemia is a common symptom observed in cardiac arrest and ischemic stroke and gives rise to an intractable damage to the cerebral neurons, which leads to disability, comatose, or even death.

Pathophysiological mechanisms involved in central nervous system diseases are diverse and complex, but it has been found that reactive oxygen species (ROS) such as free radicals play an important role in central nervous system diseases, e.g., ischemic stroke, Alzheimer's disease and Parkinson's disease. Namely, it has been proposed that various kinds of ROS generated by oxidative stress induce damage to certain nerve cells in acute and chronic degenerative neuronal diseases. Recently, it has been reported that brain damage by ischemic stroke is caused by free radicals generated by ischemia and reperfusion (Koroshetz & Moskowitz, *Trends Neurosci.* 17:227, 1996).

Free radicals are also responsible for the loss of certain nerve cells observed in Alzheimer's disease. One of the representative clinical manifestations of Alzheimer's disease is senile plaques formed through aggregation of beta-amyloid ($A_\beta$) protein. The aggregated beta-amyloid protein causes hydrogen peroxide to accumulate in nerve cells, which leads to oxidative and peroxidative reactions. Further, these reactions promote the generation of nitric oxide, and the nitric oxide thus generated reacts with a superoxide anion radical to form peroxynitrite with very strong reactivity, which results in increasing radical toxicity.

Likewise, the generation of hydroxyl radical, a strong neurotoxic mediator, by oxidative stress is believed to lead to Parkinson's disease (Ebadi et al., *Prog. Neurobiol.* 48:1, 1996). Furthermore, it has been suggested that ROS play an important role in excitotoxic neuronal cell death that is caused by glutamate excessively released in acute brain damage and chronic neurodegenerative diseases (Choi, *Neuron* 1:623, 1988).

Thus, ROS generated by the oxidative stress is directly or indirectly involved in various acute and neudegenerative diseases, e.g., brain ischemia, Alzheimer's disease, Parkinson's disease, and therefore, anti-oxidative substances are being actively investigated for the prevention and treatment of such nerve diseases.

The present inventors have endeavored to find a naturally occurring substance with anti-oxidative activity, and found that an extract of *Opuntia ficus-indica* (Linné) Mill has significantly strong anti-oxidative activity for protecting nerve cells.

*Opuntica ficus-indica* has been widely used as a folk remedy for treating burn, edema, indigestion and bronchial asthma, and it has been known that an ethanol extract of *Opuntica ficus-indica* fruit and stem shows various efficacies for protecting gastric mucosa, lower blood glucose levels and enhance immunity by analgesic and anti-inflammatory actions (Trejo-Gonzalez et al., *J. Ethnopharmacol.* 55:27-33, 1996; Ahn, *Illustrated book of Korean medical herbs* Kyohaksa, 497, 1998; Galati et al., *J. Ethnopharmacol.* 76:1-9, 2001). Recently, it has been also reported that *opuntica ficus-indica* inhibits tyrosinase which is involved in melanin synthesis (Lee N. H. et al., *J. Pharmacognosy* 31:412, 2000).

However, there is no report that an ethyl acetate extract of the stem, fruit or processed fruit of *Opuntia ficus-indica* or a compound isolated therefrom shows anti-oxidative activity for protecting nerve cells, and accordingly, the present invention discloses for the first time that such an extract can be effectively used for preventing and treating chronic nerve diseases such as ischemic stroke and Alzheimer's disease, and cardiac ischemia such as myocardial infarction.

SUMMARY OF THE INVENTION

Accordingly, a primary object of the present invention is to provide a therapeutic use of an extract of *Opuntia ficus-indica* or a compound isolated therefrom showing anti-oxidative activity for the prevention and treatment of ischemic diseases, cerebral nerve system diseases or cardiovascular system diseases.

In accordance with one aspect of the present invention, there is provided an ethyl acetate extract of *Opuntia ficus-indica* showing anti-oxidative activity for protecting nerve cells.

In accordance with another aspect of the present invention, there is provided a compound isolated from the ethyl acetate extract of *Opuntia ficus-indica* and a method for preparing same.

In accordance with still another aspect of the present invention, there is provided a pharmaceutical composition comprising the ethyl acetate extract of *Opuntia ficus-indica* or a compound isolated therefrom as an effective component, which can be used for the prevention and treatment of ischemic diseases, cerebral nerve system diseases or cardiovascular system diseases.

In accordance with still another aspect of the present invention, there is provided a use of the ethyl acetate extract of *Opuntia ficus-indica* or the compound isolated therefrom for the prevention and treatment an ischemic disease, a cerebral nerve system disease or a cardiovascular system disease.

BRIEF DESCRIPTION OF THE DRAWINGS

The above and other objects and features of the present invention will become apparent from the following description of the invention, when taken in conjunction with the accompanying drawings which respectively show.

DETAILED DESCRIPTION OF THE INVENTION

Figure 1:
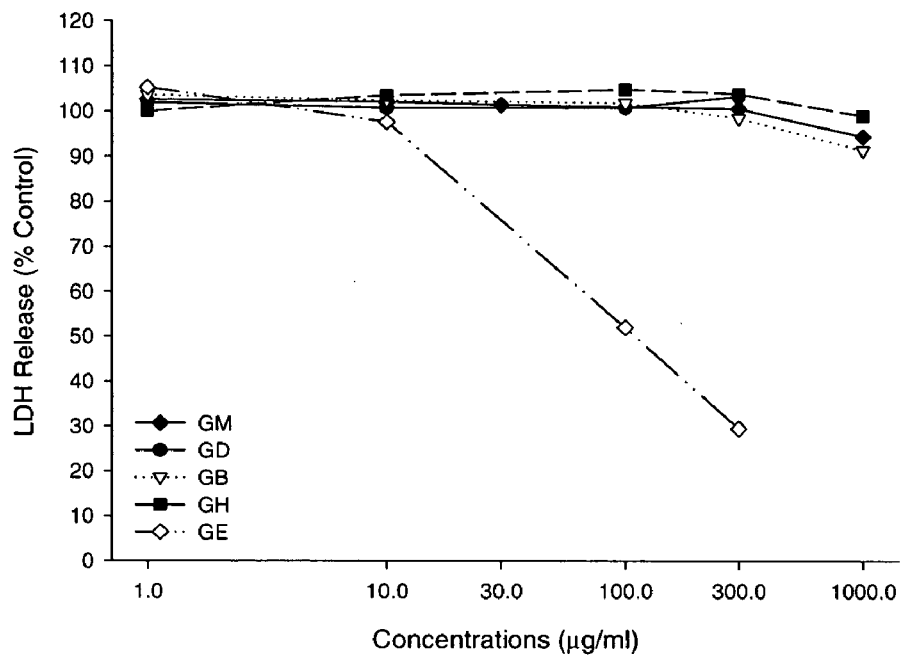
FIG. 1: inhibitory effects of various fractions extracted from *Opuntia ficus-indica* fruit on xanthine/xanthine oxidase-induced neurotoxicity.

The present invention provides a pharmaceutical composition for preventing and treating ischemic diseases, brain diseases or cardiovascular system diseases, which comprises an ethyl acetate extract of *Opuntia ficus-indica*; or any one of compounds selected from the group consisting of kaempferol of formula (1), dihydroquercetin of formula (2) and quercetin 3-methyl ether of formula (3), and their pharmaceutically acceptable salts, hydrates, solvates, isomers and a mixture thereof.

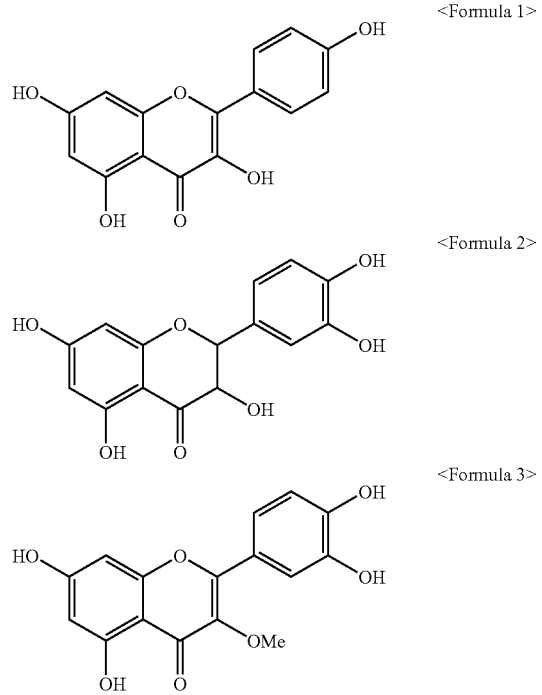

<Formula 1>

<Formula 2>

<Formula 3>

Since compounds of formula 1 to 3 may have an asymmetric carbon center within their structure, they may exist in the form of enantiomer, diasteromer or a mixture thereof containing racemate, and accordingly, these isomers of the mixture thereof are included in the scope of the present invention.

The inventive compounds are capable to also form pharmaceutically acceptable salts. These pharmaceutically acceptable salts include, but are not limited to, an inorganic base such as alkali metal hydrate (e.g., sodium hydroxide, potassium hydroxide), alkali metal bicarbonate (e.g., sodium bicarbonate, potassium bicarbonate), alkali metal carbonate (e.g., sodium carbonate, potassium carbonate, calcium carbonate) and an organic base such as a primary, secondary and tertiary amine amino acid.

Further, the inventive compounds can exist in the form of solvates, especially a hydrate. Hydration may occur either during isolation or by their hygroscopicity in the course of time. Such salts and hydrates are included in the scope of the invention.

An extract of *Opuntia ficus-indica* having protective activity for nerve cells can be prepared by extracting the fruit, stem or steam-dried fruit of *Opuntia ficus-indica* with ethyl acetate, for example, by the steps of: finely chopping the fruit, stem or steam-dried fruit of *Opuntia ficus-indica*; soaking in 0.1 to 10 l, preferably 0.5 to 7 l of a $C_{1-3}$ alcohol, e.g., methanol and ethanol, or an aqueous solution of $C_{1-3}$ alcohol per kg of said chopped *Opuntia ficus-indica* at room temperature for 4 to 5 days to obtain an extract mixture; filtrating the mixture and removing the alcohol from the filtrate to obtain an alcohol extract; adding 0.1 to 10 l, preferably 1 to 4 l of water to 1 kg of said alcohol extract; and extracting the resulting aqueous solution with 0.1 to 5 l, preferably 0.5 to 2 l of ethyl acetate (EtOAc) to obtain an ethyl acetate extract. It is also possible to directly extract the fruit, stem or steam-dried fruit of *Opuntia ficus-indica* with ethyl acetate to obtain a similar extract.

The inventive ethyl acetate extract of the fruit, stem or steam-dried fruit of *Opuntia ficus-indica* shows high activity in: clearing DPPH (1,1-diphenyl-2-picrylhydrazyl) radicals; inhibiting xanthine/xanthine oxidase-induced neurotoxicity; and suppressing hydrogen peroxide-induced neurotoxicity. Such activity of the ethyl acetate extract of *Opuntia ficus-indica* is unique in that other extracts, e.g., $CH_2Cl_2$ and BuOH extracts thereof, are essentially inactive.

Thus, the ethyl acetate extract of *Opuntia ficus-indica* is an efficient ROS scavenging agent and can be used for the purpose of preventing and treating cerebral nerve cell damage caused by brain diseases such as Alzheimer's disease, stroke and Parkinson's disease; and myocardial infarction by preventing myocardiac damage from cardiac ischemia.

From the inventive ethyl acetate extract of *Opuntia ficus-indica*, active compounds for protecting neurons can be isolated by way of performing column chromatography using a silica gel, Sephadex LH-20, RP-18, polyamide, Toyoperl or XAD resin column. The use of a Sephadex LH-20, RP-18 or silica gel column is preferred.

As the result, 3-oxo-α-ionol β-D-glucoside, kaempferol, dihydrokaempferol, kaempferol 3-methyl ether, quercetin, dihydroquercetin and quercetin 3-methyl ether have been isolated from the inventive ethyl acetate extract of *Opuntia ficus-indica*. 3-Oxo-α-ionol β-D-glucoside, kaempferol 3-methyl ether and quercetin 3-methyl ether are isolated from *Opuntia ficus-indica* for the first time in the present invention.

Kaempferol, quercetin, dihydroquercetin and quercetin 3-methyl ether effectively inhibit nerve cell damage induced by hydrogen peroxide as well as xanthine/xanthine oxidase, and show high DPPH radical scavenging activity. The compound showing the highest inhibitory activity for xanthine/xanthine oxidase or hydrogen peroxide-induced neurotoxicity is quercetin 3-methyl ether, while quercetin, dihydroquercetin and kaempferol also exhibit significant activities. Therefore, it has been confirmed that the effective components of the ethyl acetate extract of *Opuntia ficus-indica* in preventing neuronal damage from xanthine/xanthine oxidase or hydroperoxide-induced neurotoxicity are kaempferol, quercetin, dihydroquercetin and quercetin 3-methyl ether.

Further, dihydroquercetin and quercetin 3-methyl ether are efficient scavengers of superoxide radicals generated by xanthine/xanthine oxidase, and effectively inhibit neuronal damage caused by NMDA. Quercetin 3-methyl ether is particularly active in protecting cerebral nerve cells in an ischemic cerebral damage animal model. Accordingly, kaempferol, dihydroquercetin, quercetin 3-methyl ether or the ethyl acetate extract of *Opuntia ficus-indica* can be advantageously used for preventing and treating neuronal damage caused by cerebral nerve system diseases such as stroke, cerebral concussion, Alzheimer's disease and Parkinson's disease; damage of neuronal cell and tissue (in particular, cerebral nerve cell and tissue) caused by ischemia; and cell damage of cardiovascular system caused by ischemia such as ischemic myocardial infarction, and can be also applied as a neuroprotective agent or a cardioprotective agent.

Pharmaceutical formulations may be prepared using the composition of the present invention according to the conventional procedures in the art. In such preparation, it is preferable to mix, dilute or encapsulate the effective ingredient with a suitable carrier in the form of capsule, sachet or other container. Therefore, the formulation of the present invention may be prepared as tablets, pills, dispersions, sachet, elixir, suspensions, emulsions, solutions, syrups, aerosols, soft or hard gelatin capsules, injection solutions or suspensions, ointments, creams or lotions.

Pharmaceutically acceptable carriers, excipients and diluents used in the inventive pharmaceutical formulations include, are not but limited to, lactose, dextrose, sucrose, sorbitol, manitol, calcium silicate, cellulose, methyl cellulose, microcrystalline cellulose, polyvinylidone, water, methyl hydroxy benzoate, propyl hydroxy benzoate, talc, magnesium stearate and mineral oil. The formulations of the present invention may further comprise fillers, anti-coagulants, lubricants, wetting agents, odoriferous substances, emulsifying agents or preservatives. The inventive pharmaceutical composition may be formulated to provide a rapid, continuous or delayed release of the effective ingredient after administering to a mammal according to the conventional procedures in the pharmaceutical field.

The inventive pharmaceutical composition can be administered orally or via parenteral routes such as percutaneous, subcutaneous, intravenous or intramuscular.

For the purpose of a clinical administration, a typical daily dose of the ethyl acetate extract of *Opuntia ficus-indica*, or kaempferol, dihydroquercetin or quercetin 3-methyl ether isolated therefrom may range from 10 to 50,000 mg/kg body weight, preferably from 50 to 1,000 mg/kg body weight and can be administered in a single dose or in divided dose. In particular, when it is administered via an intravenous or intramuscular injection, the typical daily dose may range from 10 to 5,000 mg/kg body weight, preferably from 150 to 3,000 mg/kg body weight, however, it can be changed into the higher or lower daily dose of the effective ingredient depending on a certain disease. Further, it should be understood that the amount of the effective ingredient actually administrated to a certain patient ought to be determined in light of various relevant factors including the kind of effective compound administered, the body weight, age, sex, health condition, diet and excretion rate of the individual patient, the chosen route of administration, the combination of drugs and the severity of the patient's symptom.

Further, for the purpose of acquiring a better result in treating ischemic diseases, the inventive extract of *Opuntia ficus-indica* or active compounds therefrom can be administered together with one or more of ingredient selected from the previously well-known nerve protective agents. Examples of nerve protective agents which can be administered together with the inventive compounds are N-acetylcysteine for increasing the glutathione concentration, nimodipine as a calcium antagonist, vitamin C and E as an antioxidant, tissue plasminogen activator as a thrombolytics, and other cerebral nerve and cardiovascular protective agents.

The formulations comprising the inventive compounds used for treating ischemic diseases may further comprise other ingredients for preventing and treating damage of nerve cell and tissue (in particular, cerebral nerve cell and cerebral tissue) caused by ischemia, or cell damage of cardiovascular system caused by ischemia.

The following Examples and Test Examples are given for the purpose of illustration only, and are not intended to limit the scope of the invention.

EXAMPLE

Reference Example 1

Measurement of DPPH Radical Scavenging Activity

The anti-oxidative activity of a test sample was represented by its electron donating ability (EDA) which was measured by a modified method of Blois (*Nature* 181:1199, 1958). Namely, a test sample was dissolved in 99.9% ethanol and diluted to a suitable concentration. 10 µl of the solution was mixed with 190 µl of a DPPH solution (1,1-diphenyl-2-picrylhydrazyl; dissolved in 99.9% ethanol), agitated for 5 sec, and reacted at 37° C. for 30 min, followed by measuring the absorbance of the mixture at 515 nm. EDA was estimated from the sample's absorbance relative to that of a control, and $IC_{50}$ representing 50% inhibitory activity was calculated therefrom.

Reference Example 2

Measurement of Superoxide Anion Radical Scavenging Activity

To estimate the scavenging activity of superoxide anion radical generated by the reaction between xanthine and xanthine oxidase (XOD), the method described by Toda et al. (*Planta, Med.* 57:8, 1991) was performed as follows:

Test sample solutions of various concentrations were each mixed with 0.1 mM xanthine, 0.1 mM EDTA, 50 µg/Ml bovine serum albumin (BSA), 25 mM nitroblue tetrazolium (NBT), 40 mM $Na_2CO_3$ and $7 \times 10^{-3}$ unit XOD to a final concentration of 200 µl and reacted at 25° C. for 20 min. 6.6 µl of 6 mM $CuCl_2$ was added to the reaction mixture to stop the reaction, and the absorbance of the reaction mixture was measured at 560 nm to determine the amount of formazane. The scavenging activity of superoxide anion radical was estimated from the absorbance relative to that of a control, and $IC_{50}$ representing 50% inhibitory activity was calculated therefrom.

Reference Example 3

Primary Culture of Rat Cerebrocortical Neurons

Neuronal cells isolated from the cerebral cortices of Sprague-Dawley rat embryos were cultured by the method described by Cho et al. (*Life Sci.* 68:1567, 2001). Namely, the cerebral cortices of Sprague-Dawley rat embryos at 16-18 days of gestation were isolated, and meninges encephali was removed therefrom using a dissecting microscope. The tissue thus obtained was separated into single cells by trituration using a Pasteur pipette in a medium (MEM, Gibco BRL) containing 25 mM glucose, 5% FBS, 5% horse serum and 2 mM L-glutamine. The separated cells were plated at a density of 4 to $5\times10^5$ cells/well on 24-well culture plates previously coated with poly-L-lysine and laminine to a concentration of 4 to $5\times10^5$ cells/well, and cultured in a 37° C. incubator under 95% $O_2$/5% $CO_2$. A portion of the culture solution was replaced with a fresh culture media twice per week, and cultures were treated with 10 μM cytosine arabinoside for 24 to 72 hours at day 7 to 9 after planting to inhibit the growth of non-neuronal cells. The cultured cells at day 10 to 14 after planting were used in experiments.

Reference Example 4

Induction of Neuronal Cell Damage by Oxidative Stress

The cultured cerebrocortical cells were washed three times with a HEPES-controlled salt solution (HCSS), and treated with serum-free MEM (MEM containing 25 mM glucose and 2 mM glutamine) comprising xanthine (0.5 mM) and xanthine oxidase (10 mU/Ml) for 10 min to induce cell damage caused by superoxide anion radical. The treated cells were repeatedly washed with HCSS, and cultured in serum-free MEM lacking xanthine/xanthine oxidase at 37° C. for 20 to 24 hours under 95% $O_2$/5% $CO_2$. Cell damage caused by hydrogen peroxide was induced by: washing the cultured cells, treating with HCCS containing 100 μM hydrogen peroxide for 5 min, washing repeatedly, replacing the culture media with serum-free MEM and further culturing for 20 to 24 hours. The cultured were pre-treated with various concentrations of a test sample for 1 hour, treated with xanthine/xanthine oxidase or hydrogen peroxide as describe above in the presence of the test sample, and further maintained for 20 to 24 hours, as above. The extent of cell damage was measured by the method described in Reference Example 5.

Reference Example 5

Measurement of Neuronal Cell Damage

The extent of damage of the cultured nerve cells treated according to the method of Reference Example 4 was examined morphologically using a phase-contrast microscope or determined by measuring the activity of lactate dehydrogenase (LDH) released into the culture media. Data were calculated as percentages of the control LDH activity in the culture medium exposed to the respective oxidative insult in the absence of test principles. The inhibitory activity of a test sample for the oxidative nerve cell damage was calculated from the amount of released LDH relative to that of an unchanged control. The measurement was repeated two to four times, and $IC_{50}$ representing 50% inhibitory concentration was calculated by nonlinear regression analysis the mean values using Prism (Graphed software Inc, USA).

Reference Example 6

Culture of Rat Cerebral Hippocampus Cells and Cortex Cells for Neurotoxicity Test The hippocampus and cortex were extracted from the cerebral tissue of 17-day old fetus of a pregnant SD rat using a microscope. The extracted hippocampus and cortex were each separated into discrete single cells using a pipette, and the cells obtained therefrom by centrifuging were inoculated into a 96-well plate coated with poly-L-lysine. Hippocampus cells were inoculated at a concentration of $2.5\times10^4$ cells/well, and cortex cells, at a concentration of $5\times10^4$ cells/well. 200 μl of Neurobasal medium (Life technologies) containing 2% B-27 supplementary nutrient, 25 M glutamate and 0.5 mM glutamine was added to each well, and the plate was incubated at 37° C. After 72 hours incubation, the medium was replaced with the same medium but lacking glutamate, and the cells were further incubated. A neurotoxicity test was performed after 7 to 10 days.

Reference Example 7

Activity for Preventing Cerebral Cells from Neurotoxic Damage Caused by NMDA

The cultured cells prepared in Reference Example 6 were treated with 100 μM NMDA (Sigma) for 2 hours to induce cerebral cell damage, with or without the presence of a fixed amount of a test sample. After 24 hours, the amount of LDH released into the culture solution was measured using an LDH measuring kit (Boehringer Mannheim).

Reference Example 8

Activity for Preventing Cerebral Cells from Neuronal Damage Caused by Growth Factor Withdrawal The cultured cells prepared in Reference Example 6 were cultured in NMDA medium containing 2% B27 supplementary nutrient, and then, the culture solution was replaced with the same NMDA medium but lacking B27 supplementary nutrient to induce cell death caused by undernutrition. After 24 hours, the amount of LDH released by cell necrosis was measured using an LDH measuring kit (Boehringer Mannheim) to quantify the extent of cell death.

Reference Example 9

Preparation of a Rat Model of Transient Focal Cerebral Ischemic Damage Caused by Middle Cerebral Artery Occlusion (MACO) and Reperfusion Male Sprague-Dawley rats (Daehan experimental animal center, Eumsung) weighing 250-300 g were used as experimental animals. Each experimental animal was anesthetized with 1.5% isoflurane (Forane®, Choong Wae Pharmaceutical Co.) using 70% nitrous oxide ($N_2O$) and 30% oxygen ($O_2$) as carrier gases, and operated by the method described by Nagasawa and Kogure (*Stroke* 20:1037, 1989) while maintaining the experimental animal's body temperature at about 37±0.5° C. using a heating pad and a heating lamp.

The cervix was incised along the midline of the neck of the anesthetized animal, and the right common carotid artery, internal carotid artery and external carotid artery were carefully separated therefrom while paying attention not to damage the nervus vagus. The common carotid artery and the external carotid artery were ligated, a 17 mm long probe was inserted into the internal carotid artery from the bifurgation point of the internal and external carotid artery, and was ligated just above the insertion site to occlude the base part of the middle cerebral artery. The probe had been previously prepared by making one end of a 4-0 nylon suture (Nitcho Kogyo Co., Ltd., Japan) into a spherical shape by heating and cutting to a length of 17 mm (the length excludes the spherical end), followed by immersing an about 7 to 9 mm long portion of the other end in a mixture of a silicone (Bayer Dental, Xantopren) and a hardening agent (Optosil-Xantopren Activator, Bayer Dental) to form a coating having a thickness of 0.3 to 0.4 mm. This coated end was inserted into the external carotid artery to block the blood flow therethrough. About 25 to 30 min after inducing cerebral ischemia, neurological deficit was measured, and the test animals showing the neurological deficit symptoms were included in the ischemic group. The neurological deficit was judged by observing whether the left forearm flexes when the rat is lifted by the tail in the air, or whether the body turns to the left either spontaneously or when lifted by its tail. After the middle cerebral artery was occluded for 120 min, a transient focal cerebral ischemic rat model was prepared by incising the suture site while the animal was under anesthesia by isoflurane, and pulling the spherical end of the probe out about 10 mm long to make it reperfused. The surgical site was then sutured, and the neurological deficit was measured after one day. The brain tissue was removed from the animal and subjected to histological staining.

About 30 min after inducing ischemia, 0.9% saline (vehicle, 1 ml/kg), or 10 mg/kg of quercetin, quercetin-3 methyl ether or dihydroquercetin was administered intraperitoneally.

Example 1

Preparation of an Extract of *Opuntia Ficus-Indica* Fruit and its Activity for Protecting Nerve Cells Fresh fruit of *Opuntia ficus-indica* (from Cheju Island, Korea, purchased at Kyeongdong market) was finely chopped, and seeds were removed therefrom. 7.8 kg of the chopped fruit was soaked in 40 l of methanol at room temperature for 4 to 5 days, and filtrated. Such extraction was conducted two more times, and the combined methanol solution was concentrated using a rotary evaporator at 40° C. to obtain a methanol extract. Then, 498 g of the methanol extract of *Opuntia ficus-indica* fruit was dissolved in 1 l of water, and the resulting aqueous solution was extracted successively with: dichloromethane ($CH_2Cl_2$, 600 Ml×3), ethyl acetate (EtOAc, 600 Ml×3) and butanol (BuOH, 600 Ml×3) to obtain. Several different solvent fractions were obtained from respective organic extracts and the final aqueous phase. The DPPH radical scavenging activity and inhibition of xanthine/xanthine oxidase-induced or hydrogen peroxide-induced neurotoxicity were measured in each fraction according to the methods described in Reference Examples 1 to 5, respectively.

Figure 2:
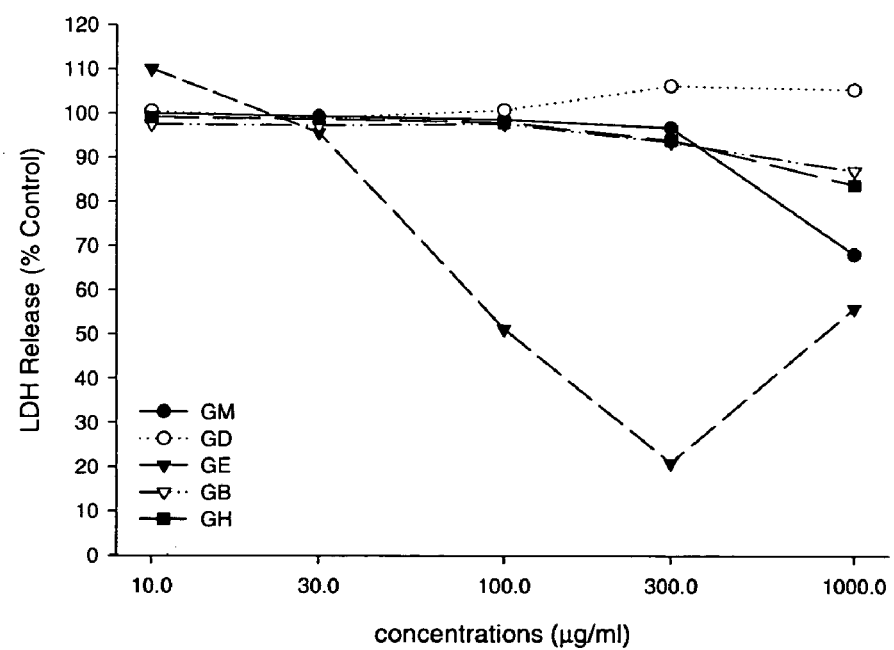
FIG. 2: inhibitory effects of various fractions extracted from *Opuntia ficus-indica* fruit on hydrogen peroxide-induced neurotoxicity.

As shown in FIGS. 1, 2 and Table 1, the dichloromethane fraction (GD), the butanol fraction (GB) and the water fraction (GH) of *Opuntia ficus-indica* fruit showed DPPH radical scavenging activity, or the inhibition of xanthine/xanthine oxidase or hydrogen peroxide-induced neurotoxicity. On the other hand, the ethyl acetate fraction (GE) effectively scavenged DPPH radicals, and significantly inhibited xanthine/xanthine oxidase-induced or hydrogen peroxide-induced neurotoxicity at $IC_{50}$: 60.0 μg/Ml, $IC_{50}$: 67.7 μg/Ml and $IC_{50}$: 115.9 μg/Ml, respectively. From these results, it has been confirmed that an ethyl acetate extract of *Opuntia ficus-indica* fruit exhibits significant neuroprotective action in cerebrocortical neurons, and accordingly, can be used for treating stroke or Alzheimer's disease.

Example 2

Preparation of an Extract of *Opuntia Ficus-Indica* Processed Fruit and its Activity for Protecting Nerve Cells 15 kg of processed fruit of *Opuntia ficus-indica* (from Cheju Island, Korea, purchased at Kyeongdong market), prepared by steaming, drying and pulverizing, was soaked in 20 l of methanol at room temperature for 4 to 5 days, and filtrated. The methanol solution was concentrated using a rotary evaporator at 40° C. to obtain a methanol extract. Then, 412 g of the methanol extract was dissolved in 1.5 l of water, and the aqueous solution was extracted successively with: dichloromethane ($CH_2Cl_2$, 800 Ml×3), ethyl acetate (EtOAc, 800 Ml×3) and butanol (BuOH, 800 Ml×3) to obtain various solvent fractions. The DPPH radical scavenging activity and inhibition of xanthine/xanthine oxidase-induced or hydrogen peroxide-induced neurotoxicity were measured in each fraction according to the methods described in Reference Examples 1 to 5, respectively.

Except for the water fraction (SH), all fractions from the processed fruit of *Opuntia ficus-indica* were active (Table 1). Among the fractions, the ethyl acetate fraction (SE) scavenged DPPH radicals most potently scavenged, and inhibited xanthine/xanthine oxidase-induced or hydrogen peroxide-induced neurotoxicity. The respective $IC_{50}$ were 58.0 μg/Ml, 22.2 μg/Ml and 21.2 μg/Ml. These results confirm that the ethyl acetate extract of *Opuntia ficus-indica* processed fruit exhibits significant neuroprotective action in cerebrocortical neurons, and accordingly, can be used for treating stroke or Alzheimer's disease.

Example 3

Preparation of an Extract of *Opuntia Ficus-Indica* Stem and its Activity for Protecting Nerve Cells 32.6 kg of fresh stem of *Opuntia ficus-indica* (from Cheju Island, purchased at Kyeongdong market) was soaked in 20 l of methanol at room temperature for 4 to 5 days, and filtrated. The methanol extraction was repeated two more times, and the combined methanol solution was concentrated using a rotary evaporator at 40° C. to obtain a methanol extract. 819.9 g of the methanol extract was dissolved in 1 l of water, and the aqueous solution was extracted successively with: dichloromethane ($CH_2Cl_2$, 600 Ml×3), ethyl acetate (EtOAc, 600 Ml×3) and butanol (BuOH, 600 Ml×3) to obtain various solvent fractions. The DPPH radical scavenging activity and inhibition of xanthine/xanthine oxidase-induced or hydrogen peroxide-induced neurotoxicity were measured in each fraction according to the methods described in Reference Examples 1 to 5, respectively.

Figure 3:
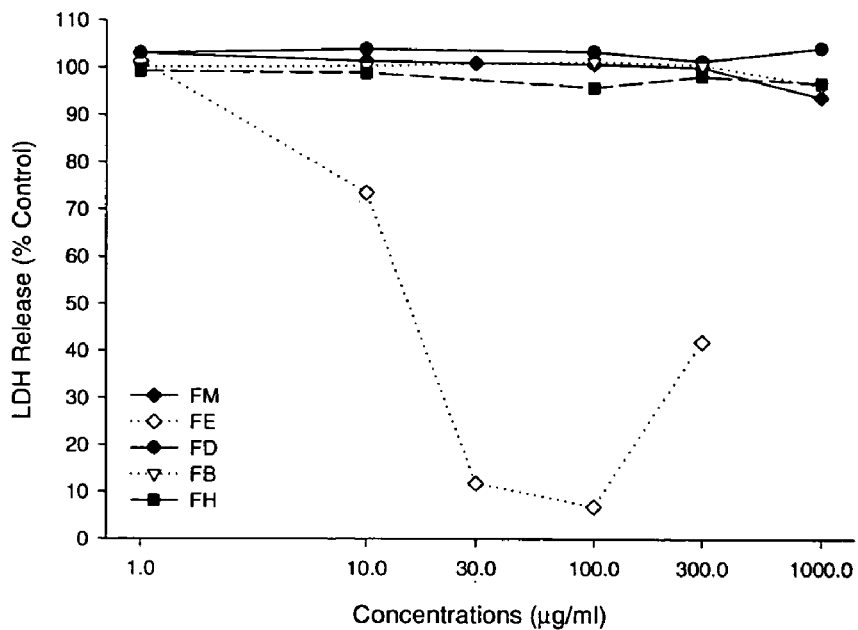
FIG. 3: inhibitory effects of various fractions extracted from *Opuntia ficus-indica* stem on xanthine/xanthine oxidase-induced neurotoxicity.
Figure 4:
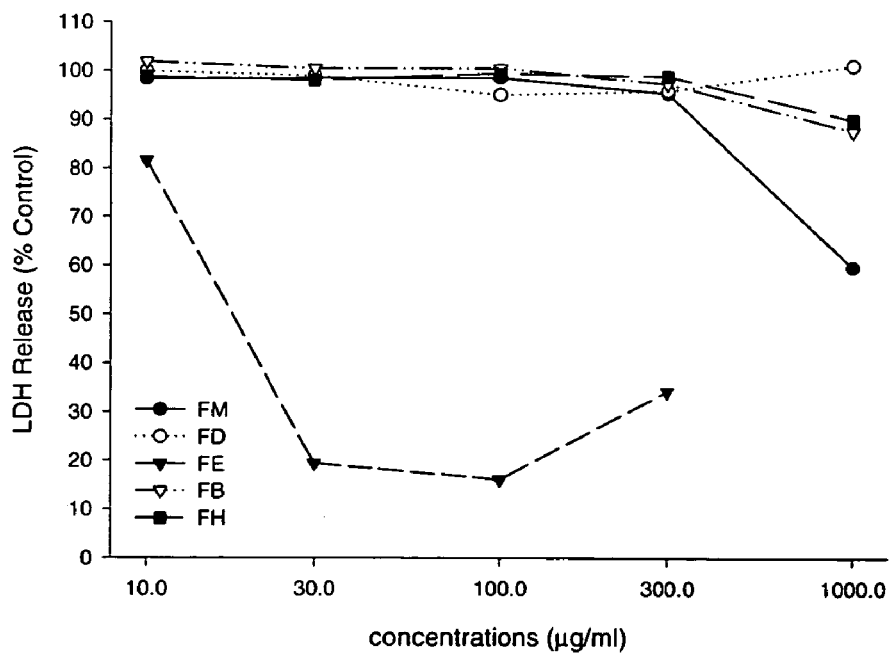
FIG. 4: inhibitory effects of various fractions extracted from *Opuntia ficus-indica* stem on hydrogen peroxide-induced neurotoxicity.

As shown in FIGS. 3, 4 and Table 1, the dichloromethane fraction (FD), the butanol fraction (FB) and the water fraction (FH) of *Opuntia ficus-indica* stem did not show the activity of DPPH radical clearance and the inhibitory activity for xanthine/xanthine oxidase or hydrogen peroxide-induced neurotoxicity at all. On the other hand, the ethyl acetate fraction (FE) significantly scavenged DPPH radicals, and potently inhibited xanthine/xanthine oxidase-induced or hydrogen peroxide-induced neurotoxicity with the respective $IC_{50}$ of 60.0 μg/Ml, 15.2 μg/Ml, and 17.5 μg/Ml. The potency of the ethyl acetate fraction (FE) from the stem in the inhibition of neurotoxicity induced by xanthine/xanthine oxidase or hydrogen peroxide was similar to that of the ethyl acetate fraction (SE) from the processed fruit, and superior to that of the ethyl acetate fraction (GE) from the fruit. These results show that the ethyl acetate extract of *Opuntia ficus-indica* stem or processed fruit exhibits significantly potent neuroprotective action in cerebrocortical neurons, and accordingly, can be used for treating the cerebral nerve system diseases such as stroke, cerebral concussion, Alzheimer's disease or Parkinson's disease.

The DPPH radical scavenging activity and the inhibition of xanthine/xanthine oxidase- or hydrogen peroxide-induced neurotoxicity by each extract fraction obtained in Examples 1 to 3 are summarized in Table 1.

Example 4

Isolation of Compounds Exhibiting Neuroprotective Activity for Nerve Cells from Ethyl Acetate Extracts of *Opuntia Ficus-Indica*

Since ethyl acetate extracts of fruit, processed fruit and stem of *Opuntia ficus-indica* show high protective activity for nerve cells, attempts to isolate compounds responsible for such activity were made as follows.

<4-1> Isolation of Compounds Having Protective Activity for Nerve Cells from the Ethyl Acetate Extract of *Opuntia Ficus-Indica* Stem 4.98 g of the ethyl acetate fraction of *Opuntia ficus-indica* stem was subjected to column chromatography (4×5 cm) using methanol as a developing solvent and Sephadex LH-20 (Cat. No. LH-20-100, Sigma) as a solid phase. After analyzing the fractions using forward phase silica gel TLC (use of dichloromethane:methanol=5:1 as a developing solvent) and reverse phase silica gel TLC (use of water:methanol=40:60 as a developing solvent), compounds having similar polarity were collected to obtain 17 subfractions (subfractions 1 to 17). Subfraction 12 having relative low polarity was subjected to reverse phase column chromatography (LiChroprep RP-18, 40 to 63 μm, 2.5×35 cm, Cat. No. 13900, Merck). The column chromatography was performed using aqueous methanol with its methanol content increasing gradually from

TABLE 1

| Solvent fraction | Activity | | |
|---|---|---|---|
| | DPPH radical scavenging activity ($IC_{50}$, μg/Ml) | Inhibition of xanthine/xanthine oxidase-induced neurotoxicity ($IC_{50}$, μg/Ml) | Inhibition of hydrogen peroxide-induced neurotoxicity ($IC_{50}$, μg/Ml) |
| Methanol extract of fruit (GM) | >500 | >1,000 | >1,000 |
| Dichloromethane fraction of fruit (GD) | 145.4 | >1,000 | >1,000 |
| Ethyl acetate fraction of fruit (GE) | 60.0 | 67.7 | 115.9 |
| Butanol fraction of fruit (GH) | 142.2 | >1,000 | >1,000 |
| Water fraction of fruit (GH) | >500 | >1,000 | >1,000 |
| Methanol extract of processed fruit (SM) | 312.6 | 600.8 | 457.6 |
| Dichloromethane fraction of processed fruit (SD) | 367.5 | 277.1 | 202.2 |
| Ethyl acetate fraction of processed fruit (SE) | 58.0 | 22.2 | 21.2 |
| Butanol fraction of processed fruit (SB) | 206.3 | 570.6 | 803.9 |
| Water fraction of processed fruit (SH) | >500 | >1,000 | 852.1 |
| Methanol extract of stem (FM) | >500 | >1,000 | >1,000 |
| Dichloromethane fraction of stem (FD) | 448.2 | >1,000 | >1,000 |
| Ethyl acetate fraction of stem (FE) | 60.0 | 15.2 | 17.5 |
| Butanol fraction of stem (FB) | >500 | >1,000 | >1,000 |
| Water fraction of stem (FH) | >500 | >1,000 | >1,000 |

40% to 60%, and the effluents were divided into 12 subfraction (sub fractions 12A to 12L) according to the polarity. Subfraction 12B was subjected to Sephadex LH-20 column chromatography (2.5×35 cm) using aqueous methanol as a developing solvent to obtain 3-oxo-α-ionol β-D-glucoside (90 mg). Pure dihydrokaempferol (30.7 mg) was isolated from subfraction 12E. Subfraction 12C was subjected to Sephadex LH-20 column chromatography (2.5×35 cm) using aqueous methanol as a developing solvent to obtain dihydroquercetin (77.5 mg). Subfraction 12I was also successively subjected to Sephadex LH-20 column chromatography under the same conditions, and to reverse phase column chromatography (LiChroprep RP-18, 40 to 63 μm, 2.5×35 cm, Cat. No. 13900, Merck) using 50% methanol, to obtain quercetin-3 methyl ether (59.3 mg). Subfraction 12K was subjected to Sephadex LH-20 column chromatography using methanol as a developing solvent, and purified by preparative RP-18 TLC (10×10 cm×0.25 cm, Cat. No. 15423, Merck, 50% MeOH) to obtain kaempferol 3-methyl ether (5.2 mg).

Further, subfraction 15 having relative low polarity was subjected to Sephadex LH-20 column chromatography (2.0× 30 cm, methanol) and preparative RP-18 TLC (10×10 cm×0.25 cm, Cat. No. 15423, Merck, 60% MeOH) to obtain kaempferol (10 mg) and quercetin (10 mg).

<4-2> Isolation of Compounds Having Protective Activity for Nerve Cells from Ethyl Acetate Extracts of *Opuntia Ficus-Indica* Fruit and Processed Fruit 1.82 g of the ethyl acetate fraction of *Opuntia ficus-indica* fruit was subjected to Sephadex LH-20 column chromatography (4.0×26.5 cm, methanol). The obtained fraction was subjected to normal phase silica gel TLC together with reverse phase silica gel TLC while changing the polarity of developing solvent. Compounds having similar polarity were collected to obtain 13 subfractions (subfractions 1' to 13'). 2.4 mg of kaempferol was isolated from subfraction 11', and 3.6 mg of quercetin, from subfraction 12'. Subfraction 8' was subjected to column chromatography (2×30 cm) using silica gel. Dihydrokaempferol (6.1 mg) was obtained when eluted with a mixture of dichloromethane and methanol (20/1) with gradually increasing the polarity. Subfraction 9' was subjected to column chromatography (1×18.5 cm) using silica gel. Dihydroquercetin (2.2 mg), kaempferol 3-methyl ether (0.6 mg) and quercetin 3-methyl ether (3.0 mg) were obtained when eluted with a mixture of dichloromethane and methanol (20/1) with gradually increasing the polarity. The ethyl acetate extract of *Opuntia ficus-indica* processed fruit was subjected to a similar isolation procedure to obtain a result similar to the result found for the ethyl acetate extract of *Opuntia ficus-indica* fruit.

Example 5

Structural Analyses of the Compounds Having Protective Activity for Nerve Cells

NMR spectra were recorded on a Bruker 300 spectrometer. $^1$H-$^1$H COSY, HMQC and HMBC NMR spectra were obtained with the usual puls sequences. $^1$H-NMR (300 MHz), $^{13}$C-NMR (75 MHz) and HMBC correlative spectral data are shown in Tables 2 and 3.

TABLE 2

| | | | | $^1$H signals (δ)* | | | |
|---|---|---|---|---|---|---|---|
| H | Kaempferol | Dihydrokaempferol | Kaempferol 3-methyl ether | Quercetin | Dihydroquercetin | Quercetin 3-methyl ether |
| 2 | | 4.99 (11.59) | | | 4.39 (11.54) | |
| 3 | | 4.55 (11.59) | | | 4.80 (11.54) | |
| 4 | | | | | | |
| 5 | | | | | | |
| 6 | 6.07 (1.72) | 5.89 (2.09) | 6.10 (1.41) | 6.07 (1.79) | 5.77 (1.79) | 6.09 (1.82) |
| 7 | | | | | | |
| 8 | 6.29 (1.82) | 5.93 (2.13) | 6.30 | 6.29 (1.72) | 5.81 (1.79) | 6.28 (1.82) |
| 9 | | | | | | |
| 10 | | | | | | |
| 1' | | | | | | |
| 2' | 7.98 (8.81) | 7.36 (8.57) | 7.89 (8.67) | 7.63 (1.75) | 6.85 (1.22) | 7.52 (1.96) |
| 3' | 6.79 (8.83) | 6.84 (8.60) | 6.82 (8.82) | | | |
| 4' | | | | | | |
| 5' | 6.79 (8.83) | 6.84 (8.60) | 6.82 (8.82) | 6.78 (8.49) | 6.69 (8.11) | 6.80 (8.38) |
| 6' | 7.98 (8.81) | 7.36 (8.57) | 7.89 (8.67) | 7.53 (8.45, 1.83) | 6.74 (8.16, 1.52) | 7.43 (8.46) |
| OMe | | | 3.67 | | | 3.68 |

*Values in parentheses are coupling constants (in Hz)

TABLE 3

| | | $^{13}$C signals | | |
|---|---|---|---|---|
| | | Kaempferol 3-methyl ether | | Quercetin 3-methyl ether |
| C | Dihydrokaempferol | HMBC | Dihydroquercetin | HMBC |
| 2 | 85.4 | 158.5 | 85.5 | 158.4 |
| 3 | 74.0 | 139.9 | 74.1 | 139.9 |
| 4 | 198.8 | 180.4 | 198.8 | 180.4 |
| 5 | 169.4 | 163.5 | 169.2 | 163.5 |

TABLE 3-continued

| | | ¹³C signals | | | |
|---|---|---|---|---|---|
| | | Kaempferol 3-methyl ether | | Quercetin 3-methyl ether | |
| C | Dihydrokaempferol | | HMBC | Dihydroquercetin | HMBC |
| 6 | 97.8 | 100.2 | C5, C7, C8, C10 | 97.7 | 100.1 C5, C7, C8, C10 |
| 7 | 165.7 | 166.5 | | 165.7 | 166.3 |
| 8 | 96.8 | 95.2 | C6, C7, C9, C10 | 96.7 | 95.1 C6, C7, C9, C10 |
| 9 | 164.9 | 158.9 | | 164.9 | 158.8 |
| 10 | 102.2 | 106.3 | | 102.2 | 106.2 |
| 1' | 129.7 | 123.0 | | 130.3 | 123.3 |
| 2' | 130.7 | 131.8 | C2, C4', C6' | 116.5 | 116.8 C2, C3', C4', C6' |
| 3' | 116.5 | 117.0 | C1', C5', C4' | 146.7 | 148.8 |
| 4' | 159.6 | 162.1 | | 147.5 | 150.3 |
| 5' | 116.5 | 117.0 | C1', C3', C4' | 116.3 | 116.8 C1', C3', C4' |
| 6' | 130.7 | 131.8 | C2, C2', C4' | 121.3 | 122.7 C2, C2', C4' |
| OMe | | 60.9 | C3 | | 60.9 C3 |

Analyses of the above result showed that respective structures of the each compound were identical with those previously reported: kaempferol (Okuyama et al., *Chem. Pharm. Bull.* 26:3071, 1978); quercetin (Grande et al., *Planta Medica.* 51:414, 1985); dihydrokaempferol (Shen et al., *Phytochemistry* 24:155, 1985); dihydroquercetin (Nonaka et al., *Chem. Pharm. Bull.* 35:1105, 1987); kaempferol 3-methyl ether (Grande et al., *Planta Medica* 51:414, 1985); quercetin 3-methyl ether (Barbera et al., *Phytochemistry* 25:2357, 1986); and 3-oxo-α-ionol β-D-glucoside (Pabst et al., *Phytochemistry* 31:1649, 1992).

Example 6

Anti-Oxidative and Neuroprotective Activity of Compounds Isolated from *Opuntia Ficus-Indica* Fruit, Processed Fruit and Stem The DPPH radical scavenging activity, superoxide anion radical scavenging activity, and inhibition of the neurotoxicity induced in cultured neurons by xanthine/xanthine oxidase, hydrogen peroxide, NMDA or growth factor withdrawal were evaluated by the methods described in Reference Examples 1 to 8, respectively.

Figure 5:
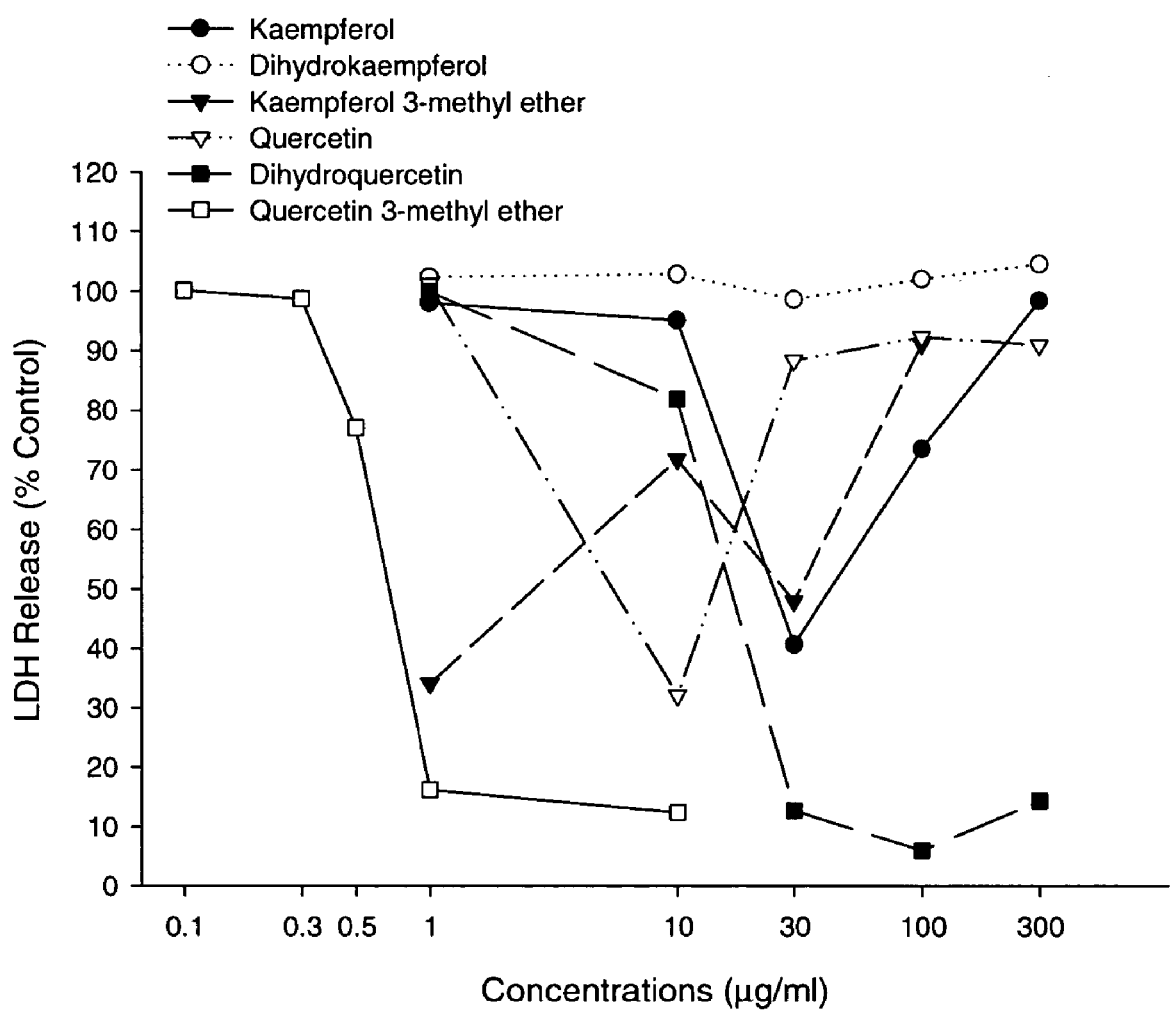
FIG. 5: inhibitory effects of the compounds isolated from an ethyl acetate extract of *Opuntia ficus-indica* on xanthine/xanthine oxidase-induced neurotoxicity.
Figure 6:
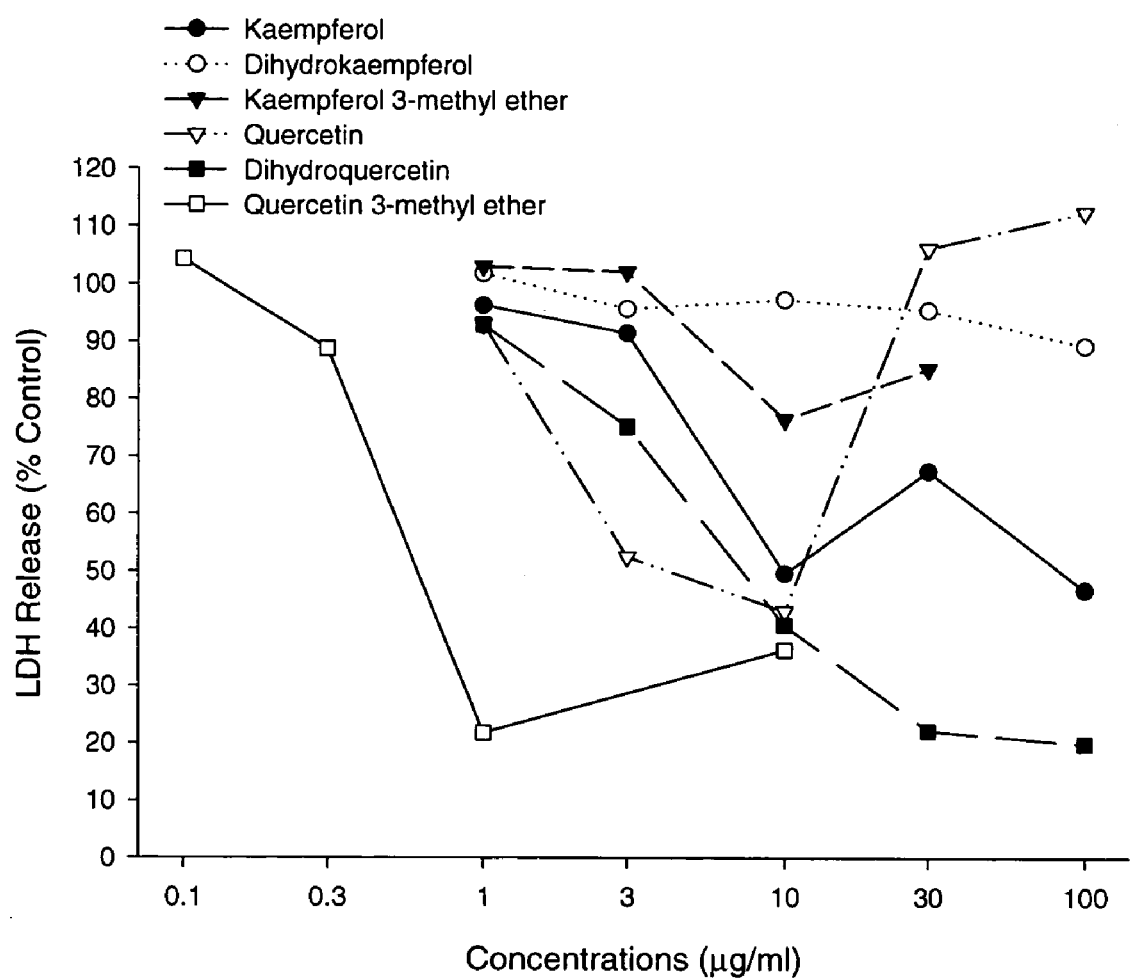
FIG. 6: inhibitory effects of the compounds isolated from an ethyl acetate extract of *Opuntia ficus-indica* on hydrogen peroxide-induced neurotoxicity.
Figure 7:
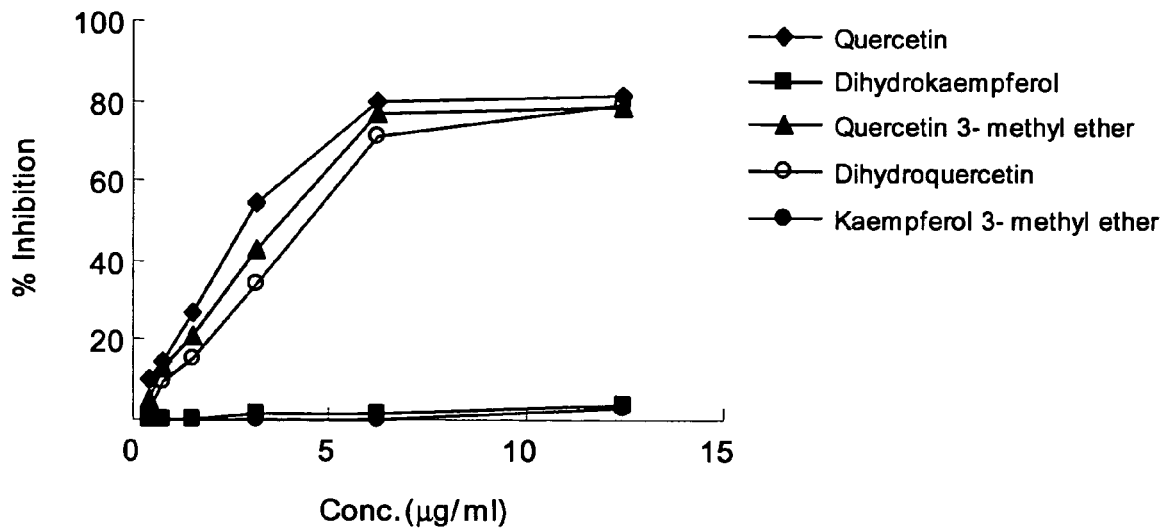
FIG. 7: DPPH radical scavenging activities of the compounds isolated from an ethyl acetate extract of *Opuntia ficus-indica*.
Figure 8:
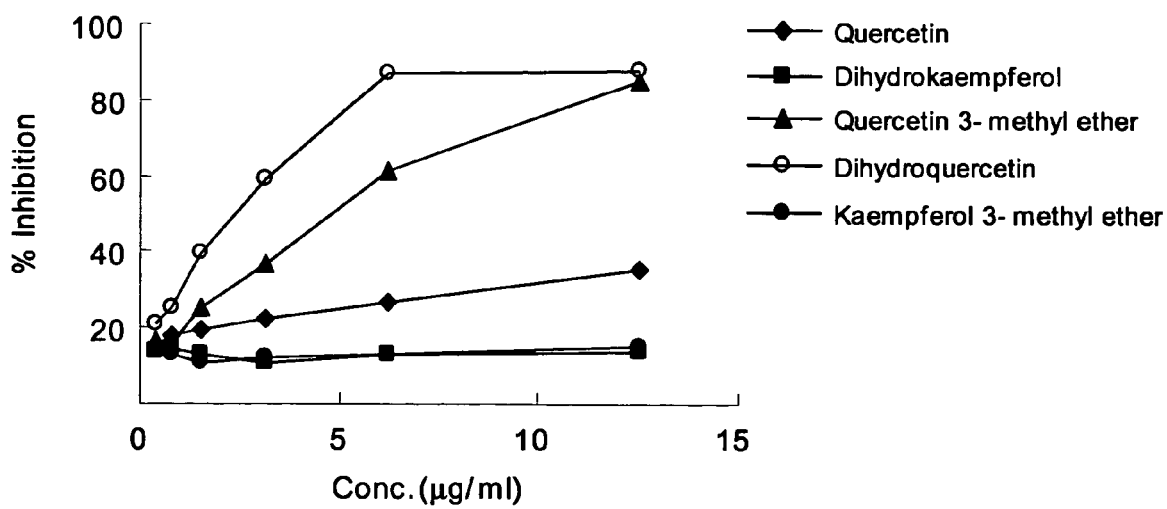
FIG. 8: superoxide anion radical scavenging activities of the compounds isolated from an ethyl acetate extract of *Opuntia ficus-indica*.
Figure 9:
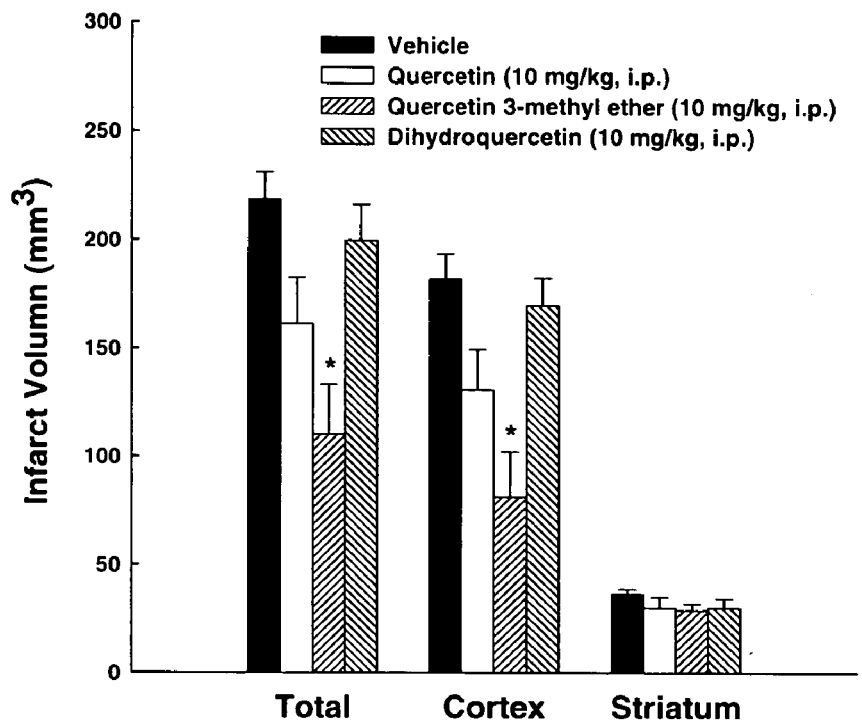
FIG. 9: effects of quercetin, quercetin 3-methyl ether and dihydroquercetin on the infarction volume of cerebral cortex, corpus striatum or the total infarction volume.
Figure 10:
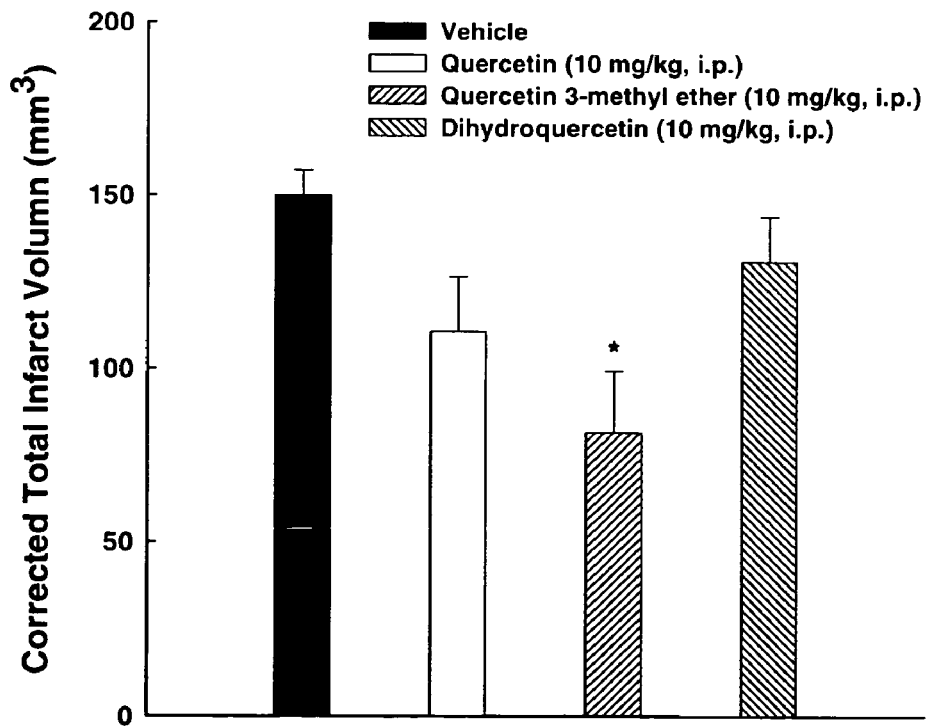
FIG. 10: effects of quercetin, quercetin 3-methyl ether and dihydroquercetin on the corrected total infarction volume.
Figure 11:
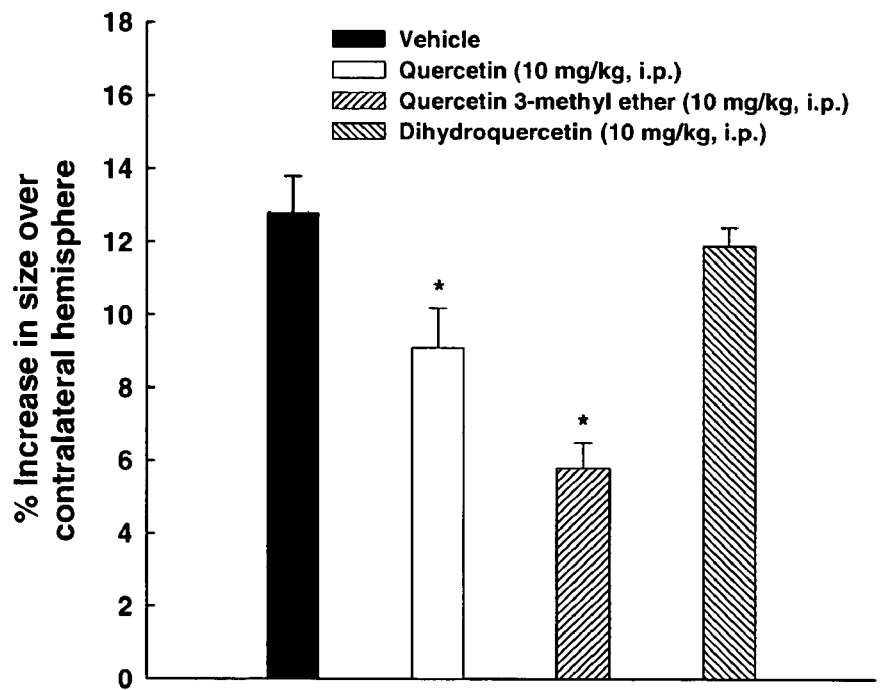
FIG. 11: effects of quercetin, quercetin 3-methyl ether and dihydroquercetin on swelling ratio.

Quercetin, dihydroquercetin and quercetin 3-methyl ether were found to show potent DPPH radical scavenging activity, and dihydroquercetin and quercetin 3-methyl ether showed potent superoxide anion radical scavenging activity from xanthine by xanthine oxidase system (Table 4). As shown in Table 5 and FIGS. 5 and 6, it has been confirmed that kaempferol, quercetin, dihydroquercetin and quercetin 3-methyl ether strongly inhibit the neurotoxicity induced by hydrogen peroxide or xanthine/xanthine oxidase. Furthermore, dihydroquercetin and quercetin 3-methyl ether were shown to inhibit the neurotoxicity induced by NMDA, and in particular, quercetin 3-methyl ether also inhibited the neurotoxicity induced by growth factor withdrawal.

TABLE 4

| | DPPH radical scavenging activity ($IC_{50}$, μg/Ml) | Superoxide anion radical scavenging activity ($IC_{50}$, μg/Ml) |
|---|---|---|
| Kaempferol | >50 | >50 |
| Dihydrokaempferol | >50 | >50 |
| Kaemferol 3-methyl ether | >50 | >50 |
| Quercetin | 2.89 | >50 |
| Dihydroquercetin | 4.49 | 2.48 |
| Quercetin 3-methyl ether | 3.76 | 4.77 |

TABLE 5

| | Inhibition of xanthine/xanthine oxidase-induced neurotoxicity ($IC_{50}$, μg/Ml) | Inhibition of hydrogen peroxide-induced neurotoxicity ($IC_{50}$, μg/Ml) | Inhibition of NMDA induced neurotoxicity | Inhibition of growth factor withdrawal-induced neurotoxicity |
|---|---|---|---|---|
| Kaempferol | 24.9 | 29.7 | — | — |
| Dihydrokaempferol | >300 | >300 | — | — |
| Kaempferol 3-methyl ether | — | >300 | — | — |
| Quercetin | 5.5 | 4.1 | — | — |

TABLE 5-continued

| | Inhibition of xanthine/xanthine oxidase-induced neurotoxicity ($IC_{50}$, μg/Ml) | Inhibition of hydrogen peroxide-induced neurotoxicity ($IC_{50}$, μg/Ml) | Inhibition of NMDA induced neurotoxicity | Inhibition of growth factor withdrawal-induced neurotoxicity |
|---|---|---|---|---|
| Dihydroquercetin | 16.6 | 7.8 | 33% inhibition (9 μg/Ml) 47% inhibition (30 μg/Ml) | — |
| Quercetin 3-methyl ether | 0.65 | 0.60 | 21% inhibition (9 μg/Ml) 54% inhibition (30 μg/Ml) | 31% inhibition (9 μg/Ml) 86% inhibition (30 μg/Ml) |

Example 7

In Vivo Neuroprotective Activity of Quercetin-3 Methyl Ether

The brain damage caused by transient focal cerebral ischemia in a rat model was measured by the TTC (2,3,5-triphenyltetrazolium chloride) staining method (Bederson et al., *Stroke* 17:1304, 1986). One day after occluding the middle cerebral artery, the rat was sacrificed using a guillotine, and the brain was removed therefrom. Brain coronal sections were prepared by successive cutting of the removed brain to a thickness of 2 mm beginning at 1 mm spot from the frontal pole using a brain matrix (ASI Instruments, Warren, Mich., USA). Each section was treated with 2% TTC solution in 0.9% saline and incubated at 37° C. for 60 min to stain. Each section stained with TTC was fixed with a phosphate-buffered formalin solution, and its reverse side image was acquired by using a computer equipped with a CCD camera. The infarction area ($cm^2$) of cerebral cortex and corpus striatum where no deep red color staining occurred was measured by using an image analysis software (Optimas, Edmonds, Wash., USA), and the infarction volume ($mm^3$) was calculated by multiplying the thickness of section. Finally, the total infarction volume was calculated as the sum of the infarction volume of the cerebral cortex and corpus striatum. At this time, a corrected infarction volume was calculated to compensate for the swelling as follows: a corrected total infarction area of each section was calculated by subtracting the normal tissue area of the right cerebral hemisphere (ipsilateral ischemic side) from the total area of the left cerebral hemisphere (contralateral non-ischemic side), and the corrected total infarction volume was calculated from the corrected total infarction area according to the same method as above.

In addition, the swelling ratio of cerebral hemisphere induced by ischemia was calculated by the following expression.

$$\text{swelling ratio (\%)} = \frac{A-B}{B} \times 100$$

A: the volume of ipsilateral ischemic cerebral hemisphere in total coronal sections ($mm^3$)
B: the volume of contralateral normal cerebral hemisphere in total coronal sections ($mm^3$)

TABLE 6

| Treatment | n | Infarction volume | | | Corrected total infarction volume | Swelling ratio (%) |
| | | Corpus striatum | Cerebral cortex | Total | | |
|---|---|---|---|---|---|---|
| Vehicle (saline) | 6 | 36.7 ± 2.0 | 181.8 ± 11.4 | 218.6 ± 12.5 | 150.0 ± 7.1 | 12.8 ± 1.0 |
| Quercetin | 9 | 30.1 ± 4.9 | 130.5 ± 18.6 | 161.1 ± 21.4 | 110.6 ± 15.8 | 9.1 ± 1.1 |
| Quercetin 3-methyl ether | 11 | 28.9 ± 3.1 | 81.2 ± 20.8* | 110.1 ± 22.9* | 81.6 ± 17.8* | 5.8 ± 0.7* |
| Dihydroquercetin | 8 | 30.1 ± 4.3 | 169.4 ± 12.7 | 199.5 ± 16.5 | 130.7 ± 13.1 | 11.9 ± 0.5 |

N: the number of tested animals
*Significant difference by the control as a result of Duncan's multiple range test Example 8

Neurological Recovery Effect of Quercetin 3-Methyl Ether

The neurological recovery effect of quercetin-3 methyl ether in the rat treated according to the method of Example 7 was examined using the method measuring a neurological score (Relton et al., *Stroke* 28:1430, 1997) as follows.

Forelimb flexion (when the rat is fully lifted by the tail in the air), duration of forelimb flexion (time of forelimb flexion over 10-second period) and symmetry of movement (when the rat is made to walk only using forelimbs while being lifted by the tail and its hindlimbs hanging in the air) were examined, and the observed scores are summarized in Table 7.

TABLE 7

| Test item | Score | | | | |
|---|---|---|---|---|---|
| | 0 | 1 | 2 | 3 | 4 |
| Forelimb flexion | No movement on left side | Limited movement on left side | Less extended or slower movement on left side | Symmetrical movement | — |
| Duration of forelimb flexion | 8-10 sec | 6-8 sec | 4-6 sec | 2-4 sec | 0-2 sec |
| Symmetry of movement | Left forelimb does not move | Left forelimb moves minimally and rat circles | Left forelimb outstretches less than right | Forelimbs outstretch and rat walks normally | — |

Figure 12:
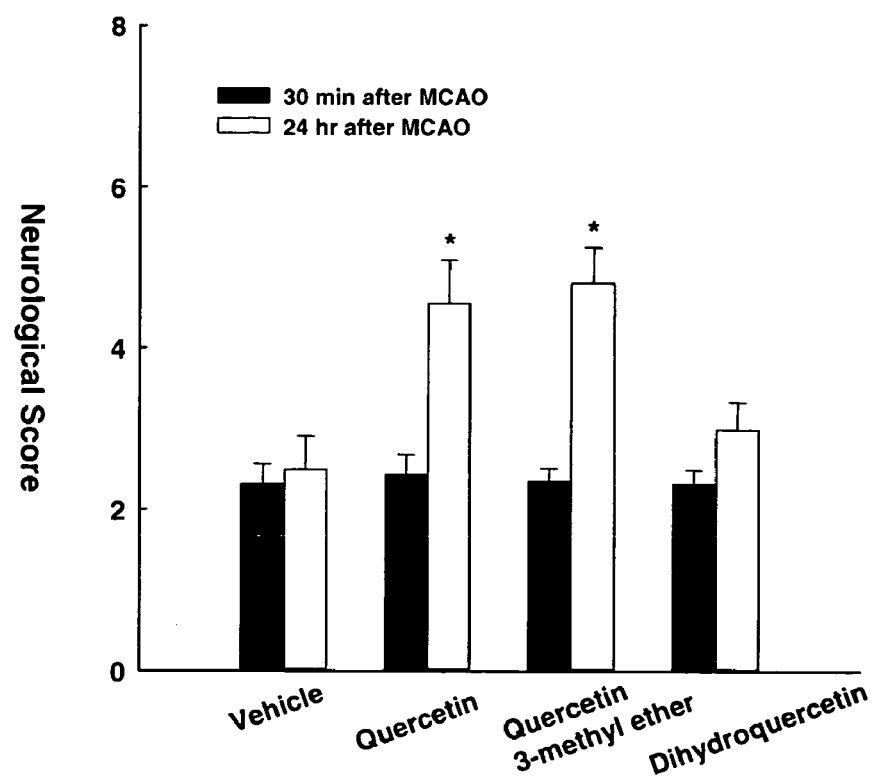
FIG. 12: effects of quercetin, quercetin 3-methyl ether and dihydroquercetin on neurological recovery.

The final neurological scores of each group are shown in Table 8 (each experimental score is shown by the format of average value±standard error) by adding up the scores shown in Table 7, and also depicted in FIG. 12. 10 point means normal (no neurological deficit), and the lower score, the larger neurological deficit.

TABLE 8

| Time until the measurement after occlusion of middle cerebral artery | Treatment | | | |
|---|---|---|---|---|
| | Vehicle (saline) | Quercetin | Quercetin 3-methyl ether | Dihydroquercetin |
| 30 min | 2.33 ± 0.24 | 2.44 ± 0.24 | 2.36 ± 0.15 | 2.33 ± 0.16 |
| 24 hour | 2.50 ± 0.41 | 4.56 ± 0.53* | 4.81 ± 0.44* | 3.00 ± 0.33 |

*Significant difference from the control at 24 hour by the Duncan's multiple range test ($p < 0.05$)

As shown in Table 8 and FIG. 12, the group treated with quercetin 3-methyl ether showed a significantly higher neurological score than the control, showing that quercetin 3-methyl ether exerts the neurological recovery effect.

While the embodiments of the subject invention have been described and illustrated, it is obvious that various changes and modifications can be made therein without departing from the spirit of the present invention which should be limited only by the scope of the appended claims.

What is claimed is:

1. A method of inhibiting nerve cell damage induced by xanthine/xanthine oxidase or hydrogen peroxidase in a nerve cell in an individual, comprising:
providing an ethyl acetate fraction of an alcohol extract of a stem, fruit or processed fruit of *Opuntia ficus-indica*,
orally or parenterally administering an effective amount of the ethyl acetate fraction of an alcohol extract of *Opuntia ficus-indica* to the individual in need thereof,
wherein the ethyl acetate fraction of an alcohol extract of *Opuntia ficus-indica* comprises quercetin 3-methyl ether as an effective ingredient, and
allowing the quercetin 3-methyl ether to inhibit nerve cell damage.

2. The method of claim 1, wherein the ethyl acetate fraction of an alcohol extract of the stem, fruit or processed fruit of *Opuntia ficus-indica* is obtained by a method comprising: 1) soaking the stem, fruit or processed fruit of *Opuntia ficus-indica* in 0.1 to 10 liter of an alcohol solvent at room temperature for 4 to 5 days to obtain an extraction mixture, 2) filtering the extraction mixture to form a filtrate, 3) removing the alcohol from the filtrate to obtain an alcohol extract, and 4) adding 0.1 to 10 liter of water to the alcohol extract and extracting an aqueous solution with 0.5 to 2 liter of ethyl acetate.

3. The method of claim 2, wherein the alcohol solvent is a $C_{1-3}$ alcohol or an aqueous solution of a $C_{1-3}$ alcohol.

4. A method of inhibiting nerve cell damage induced by xanthine/xanthine oxidase or hydrogen peroxidase in a nerve cell in an individual, comprising:
providing quercetin 3-methyl ether,
orally or parenterally administering an effective amount of the quercetin 3-methyl ether to the individual in need thereof, and
allowing the quercetin 3-methyl ether to inhibit nerve cell damage.

5. The method of claim 1, wherein the alcohol is a $C_{1-3}$ alcohol or an aqueous solution of a $C_{1-3}$ alcohol.

6. The method of claim 1, wherein the alcohol is methanol.

7. The method of claim 1, wherein the ethyl acetate fraction of an alcohol extract of *Opuntia ficus-indica* is administered in a range from 10 to 50,000 mg/kg body weight in a single dose or in divided doses.

8. The method of claim 4, wherein the quercetin 3-methyl ether is administered in a range from 10 to 50,000 mg/kg body weight in a single dose or in divided doses.

9. The method of claim 1, wherein the administering is parenteral administration.

10. The method of claim 1, wherein the administering is oral administration.

11. The method of claim 4, wherein the administering is parenteral administration.

12. The method of claim 4, wherein the administering is oral administration.

13. The method of claim 9, wherein the parenteral administration is subcutaneous, intravenous, or intramuscular administration.

14. The method of claim 11, wherein the parenteral administration is subcutaneous, intravenous, or intramuscular administration.

* * * * *

UNITED STATES PATENT AND TRADEMARK OFFICE
CERTIFICATE OF CORRECTION

PATENT NO. : 7,563,467 B2  
APPLICATION NO. : 10/493748  
DATED : July 21, 2009  
INVENTOR(S) : Yong Sup Lee et al.

Page 1 of 1

It is certified that error appears in the above-identified patent and that said Letters Patent is hereby corrected as shown below:

On the title page, item (75), line 5, "Yunaaon" should read --Yunseon--.

Signed and Sealed this

Twenty-second Day of September, 2009

David J. Kappos
*Director of the United States Patent and Trademark Office*